United States Patent [19]

Yoshiyama

[11] Patent Number: 4,834,943
[45] Date of Patent: May 30, 1989

[54] APPARATUS FOR THE PREPARATION OF OBJECTS FOR MICROSCOPIC EXAMINATION

[75] Inventor: Eiichi Yoshiyama, Nagano, Japan

[73] Assignees: Kabushiki Kaisha Tiyoda Seisakusho, Nagano; Sakura Seiki Kabushiki Kaisha, Tokyo, both of Japan

[21] Appl. No.: 57,524

[22] PCT Filed: Sep. 19, 1986

[86] PCT No.: PCT/JP86/00488

§ 371 Date: Jul. 16, 1987

§ 102(e) Date: Jul. 16, 1987

[87] PCT Pub. No.: WO87/01803

PCT Pub. Date: Mar. 26, 1987

[30] Foreign Application Priority Data

Sep. 20, 1985 [JP] Japan ................................ 60-206578

[51] Int. Cl.⁴ ............................................. G01N 1/28
[52] U.S. Cl. ......................................... 422/62; 422/99; 435/284; 435/287; 118/429; 118/500
[58] Field of Search ............................ 422/62, 99, 64; 435/284, 287, 285; 118/429, 500

[56] References Cited

U.S. PATENT DOCUMENTS

| | | | |
|---|---|---|---|
| 4,155,978 | 5/1979 | Naono et al. | 422/64 |
| 4,234,540 | 11/1980 | Ginsberg et al. | 422/64 |
| 4,260,580 | 4/1981 | Sindo et al. | 422/64 |
| 4,569,647 | 2/1986 | McCormick | 425/117 |
| 4,668,476 | 5/1987 | Bridgham et al. | 422/62 |

Primary Examiner—Barry S. Richman
Assistant Examiner—Timothy M. McMahon
Attorney, Agent, or Firm—Ladas & Parry

[57] ABSTRACT

Apparatus for the preparation of resin-impregnated specimens for microscopic examination, comprising a stack of embedding boxes 62 each containing a specimen. A variety of reagents required for the preparation of the specimens are selectively fed to the stack of embedding boxes by a delivery pump 13. The reagent fed to the stack of embedding boxes is shaked by a reagent shaker mechanism 14 for ready infiltration into the specimens.

9 Claims, 4 Drawing Sheets

APPARATUS FOR THE PREPARATION OF OBJECTS FOR MICROSCOPIC EXAMINATION

TECHNICAL FIELD

This invention relates to apparatus for the preparation of objects for study under the electron and other type of microscope in medical and other fields of science, such that specimens such as those extracted from living matter are automatically fixed and embedded in resin material with use of minimal amounts of reagents.

BACKGROUND ART

Objects of microscopic examination in medical and other fields of science require pretreatment with reagent and embedment or infiltration of resins into the specimens for solidification. The embedded specimens are sectioned, and the sections are mounted on glass slides for optical microscopy and on mesh grids for electron microscopy.

Heretofore, for automatically embedding objects as above stated, apparatus has been used which comprises a plurality (e.g. 20) of reagent and resin containers, each in the form of an upstanding, open-top, bottomed cylinder, in annular arrangement. Embedding boxes containing objects of microstopic study have been dipped successively in the reagent and resin containers. The embedding boxes have been suspended from the periphery of a disc which is centrally supported by a rotary, vertically reciprocable post disposed at the center of the annular row of reagent and resin containers. The disk is moved up and down and rotated at intervals for dipping the embedding boxes in the successive containers.

The micrologist has, however, experienced some inconveniences with the foregoing prior art apparatus. Objects of microscopic study to be embedded are as small in size as from 0.5 by 0.5 millimeters (mm) to 1.0 by 1.0 mm. The embedding boxes for immersing such objects in required reagents are each approximately 10 mm in diameter. Nevertheless, from about 20 to 30 cubic centimeters (cc) of each reagent is required for processing a batch of, say, 20 objects. The used reagents must be discarded, and fresh supplies of reagents must be used for processing another batch. However, since some reagents are expensive, it is uneconomical to discard the considerable amounts of them each time one batch of objects is treated.

Another weakness of the prior art is that the embedding boxes holding the specimens are merely immersed in the liquid. This conventional method fails to realize ready infiltration of the liquid into the specimens.

A further drawback of the prior art manifests itself when, in the course of embedment, the specimens are immersed in alcohol of progressively higher concentrations, from about 50% up to 100%. The known apparatus has necessitated the provision of a series of five separate containers for 50%, 70%, 80%, 95% and 100% alcohol. Alcohol preparations of 50% and 100% concentrations are available on the market, but the micrologist has had to take the trouble of himself preparing the other concentrations.

The present invention aims at the elimination of all the foregoing inconveniences.

DISCLOSURE OF THE INVENTION

The apparatus for the preparation of objects for microscopic examination in accordance with the invention comprises a reagent select mechanism for selectively communicating a plurality of reagent receptacles, containing reagents for the embedment of specimens, with a delivery conduit having a delivery pump capable of bidirectional rotation and of blocking the flow of any selected reagent therethrough when out of rotation, and an embedding box holder for holding a stack of embedding boxes each in the form of a short tube having a mesh bottom for holding thereon a specimen to be embedded. The embedding boxes are stacked with their peripheries in fluid-tight engagement with each other. The embedding box holder has a bottom fitting for communicative connection with one end of the delivery conduit, and a top fitting for communicative connection with one end of an overflow conduit leading to a waste receptacle. The waste receptacle communicates with one of several ports of the reagent select mechanism via a waste conduit.

Upon loading of the embedding boxes, containing the specimens to be embedded, on the embedding box holder, the delivery pump is to be set into operation for feeding a selected reagent from one of the reagent receptacles into the embedding boxes within the holder via the delivery conduit, thereby flooding the specimens within the embedding boxes with the reagent. The delivery pump is to be held out of motion during the subsequent immersion of the specimens in the reagent. The reagent select mechanism is actuated at the same time to establish communication between the delivery conduit and waste conduit while the delivery pump is out of motion.

Upon completion of the specimen immersion for a required length of time, the delivery pump may be set into rotation in a reverse direction for discharging the used reagent into the waste receptacle.

Following the discharge of the used reagent, the reagent select mechanism may be re-actuated to place the delivery conduit in communication with another reagent receptacle containing the next reagent to be supplied. Then the delivery pump may again be set into rotation in a forward direction for delivering the next selected reagent into the embedding boxes.

The foregoing cycle of operation may be repeated for embedding the specimens within the embedding boxes. For treating the specimens with alcohol of successively higher concentrations, the lowest concentration (50%) alcohol may first be pumped into the embedding boxes. Then, with this lowest concentration alcohol left undischarged, the highest concentration (100%) alcohol may be pumped into the embedding boxes thereby gradually increasing the alcohol concentration therein.

BEST MODE FOR CARRYING OUT THE INVENTION

Figure 1:
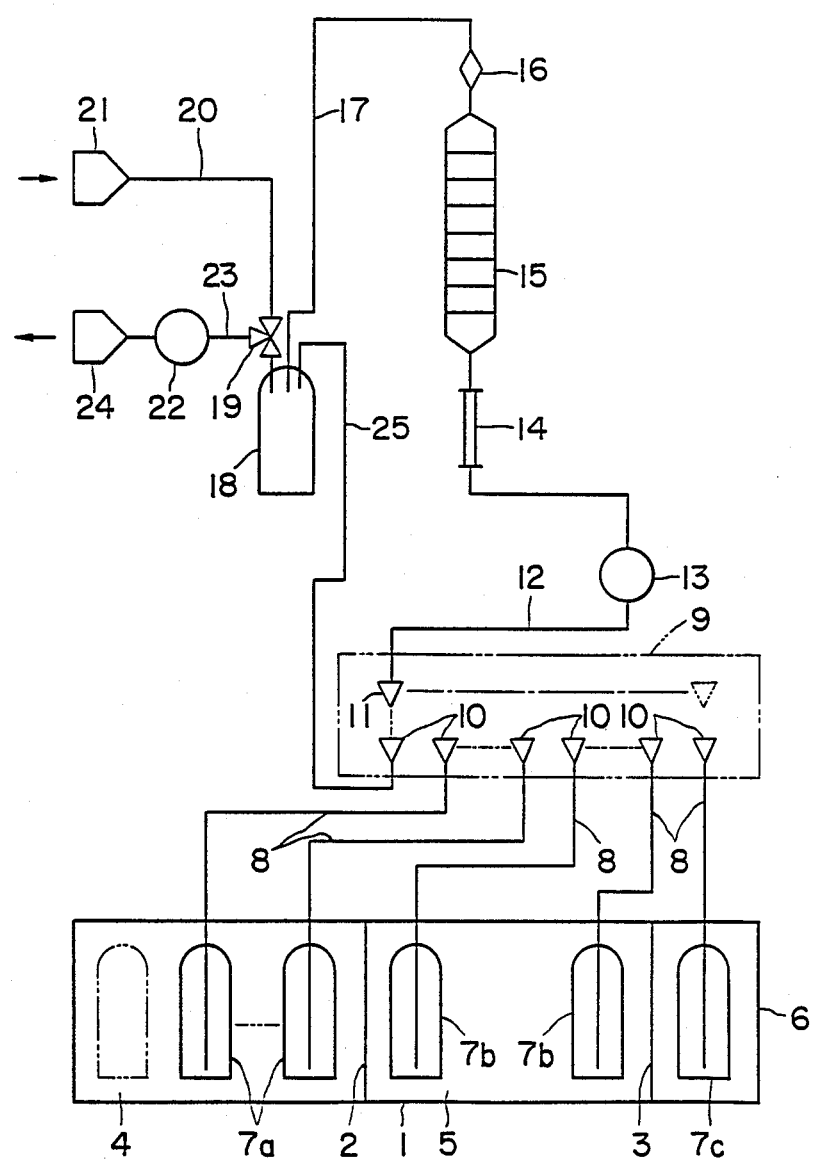
FIG. 1 is a diagram of the general organization of the apparatus for the preparation of objects for microscopic examination in accordance with the invention.

With reference to FIG. 1, a diagrammatic illustration of the general organization of the apparatus in accordance with the invention, there is provided at 1 a reagent housing which is provided with partitions 2 and 3 for dividing its interior into three chambers 4, 5 and 6. Each of these chambers accommodates one or more reagent receptacles 7a, 7b and 7c. The reagent receptacles 7a in the chamber 5 contain reagents such as glutaraldehyde, sodium acetate, etc., which are being held at a relatively low temperature of, for example, 4° C. The reagent receptacles 7b in the chamber 5 contain, for example, a 50% alcohol solution and 100% alcohol at room temperature. The single reagent receptacle 7c in the chamber 6 contains, for example, a resin at a temperature of approximately 37° C.

Inserted respectively in the reagent receptacles 7a, 7b and 7c are suction conduits 8 having their open bottom ends held close to the bottoms of the reagent receptacles. The suction conduits 8 communicate the reagent receptacles 7a, 7b and 7c with respective female coupling members 10 of a reagent select mechanism 9. In addition to the female coupling members 10, which are held in fixed locations, the reagent select mechanism 9 comprises a single male coupling member 11 movable into fluid-tight engagement with any selected one of the female coupling members.

A delivery conduit 12 has its lower end communicatively affixed to the male coupling member 11 and extends upwardly therefrom. The delivery conduit 12 is provided both with a delivery pump 13 for forcing a required reagent up through the delivery conduit from the male coupling member 11, and with a shaker mechanism 14 for imparting vibration to the reagent being delivered. The upper end of the delivery conduit 12 is communicatively coupled to the bottom end of an embedding box holder 15 in which is held a stack of embedding boxes containing objects of microscopic examination to be embedded. The delivery pump 13 should be bidirectional and, when out of motion, should block the flow of the liquid therethrough. The shaker mechanism 14 operates, when the delivery pump 13 is out of motion following the delivery of a desired reagen into the embedding case holder 15, to agitate or shake the reagent on the downstream side of the shaker mechanism and hence to assure intimate contact of the reagent with the specimens in the embedding cases.

The embedding box holder 15 has its top end communicatively coupled to an overflow conduit 17. The embedding box holder 15 communicates with the overflow conduit 17 via an enlargement 16 providing a space into which part of the reagent on the downstream side of the shaker mechanism 14 can flow during the above described operation of the shaker mechanism.

The overflow conduit 17 communicates with a waste receptacle 18, which may be contained in the chamber 4 of the reagent housing 1. Also communicating with the waste receptacle 18 is an air intake conduit 20 having an air filter 21 on its end away from the waste receptacle. The air intake conduit 20 is further provided with a three-way valve 19 for selectively placing the waste receptacle 18 in and out of communication with the air intake conduit 20 and with an exhaust conduit 23. A vacuum pump 22 is provided to the exhaust conduit 23 for the discharge of exhaust gases via an activated charcoal filter 24. The waste receptacle 18 further communicates by way of a waste liquid conduit 25 with one of the female coupling members 10 of the reagent select mechanism 9. Notwithstanding the showing of FIG. 1, the air filter 21 is dispensable, and the conduit 20 may be used for communicating the waste receptacle 18 with the activated charcoal filter 24 or with the reagent receptacles.

Given hereafter is a more detailed discussion of the reagent select mechanism 9, shaker mechanism 14 and embedding box holder 15 which are incorporated in the micrological apparatus of the foregoing general configuration in accordance with the invention.

Figures 2, 3:
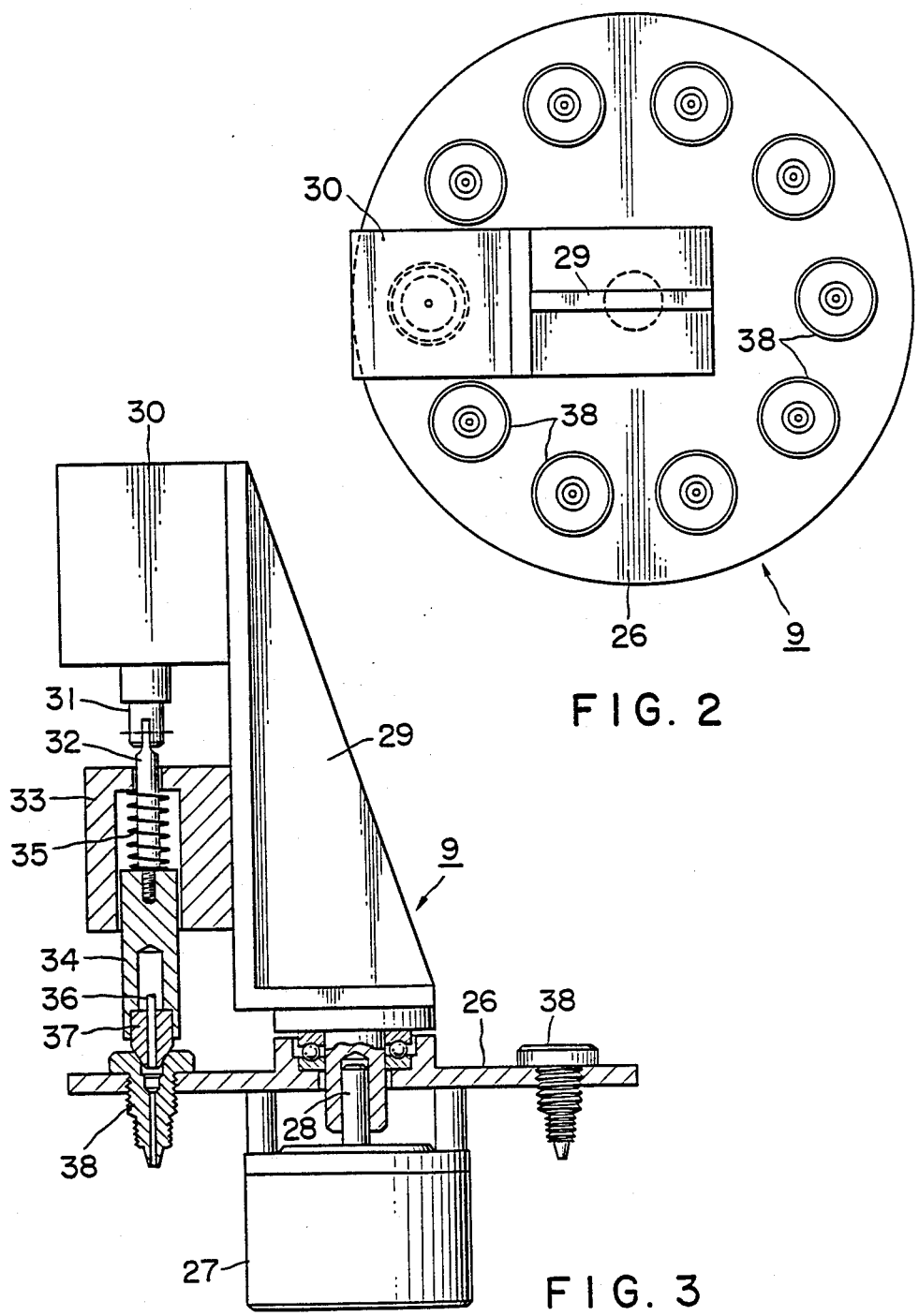
FIG. 2 is a top plan view of the reagent select mechanism.
FIG. 3 is a side elevation, partly in section, of the reagent select mechanism.

As illustrated in detail in FIGS. 2 and 3, the reagent select mechanism 9 comprises a table 26 of circular shape. Rigidly mounted on the underside of the table 26 in alignment therewith is an electric drive motor 27 having a drive shaft 28 coupled to a rotary post 29 which is rotatably supported over the table. A solenoid 30 is secured to one side of the rotary post 29 at or adjacent the top end therof. The depending plunger 31 of the solenoid 30 is coupled to one end of an upright connecting rod 32, the other end of which is secured to a reciprocator 34. This reciprocator is movable up and down as guided by a guide 33 secured to the rotary post 29 in an underlying relation to the solenoid 30. A helical compression spring 35 acts between guide 33 and reciprocator 34 for biasing the latter downwardly. The reciprocator 34 has rigidly mounted to its bottom end a plug 37 having its bottom end portion formed into frustoconical shape to serve as the noted male coupling member 11, FIG. 1, of the reagent select mechanism 9. In constant communication with the delivery conduit 12, FIG. 1, a pipe 36 extends through the plug 37.

Rigidly mounted to the table 26 are a plurality of socket members 38 which correspond to the female coupling members 10, FIG. 1, of the reagent select mechanism 9 and which are arranged in an annular row along the periphery of the table 26 in concetric relation thereto. As will be seen by referring back to FIG. 1, each socket member 38 has coupled thereto one of the suction conduits 8, which are in communication with the reagent receptacles 7a, 7b and 7c, or the waste liquid conduit 25 in communication with the waste receptacle 18.

Figure 4:
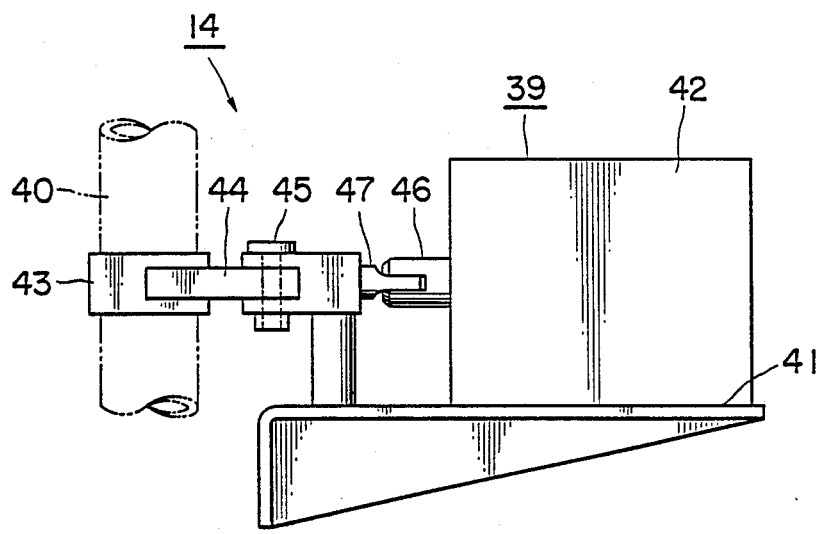
FIG. 4 is a side elevation of a shaker mechanism.
Figure 5:
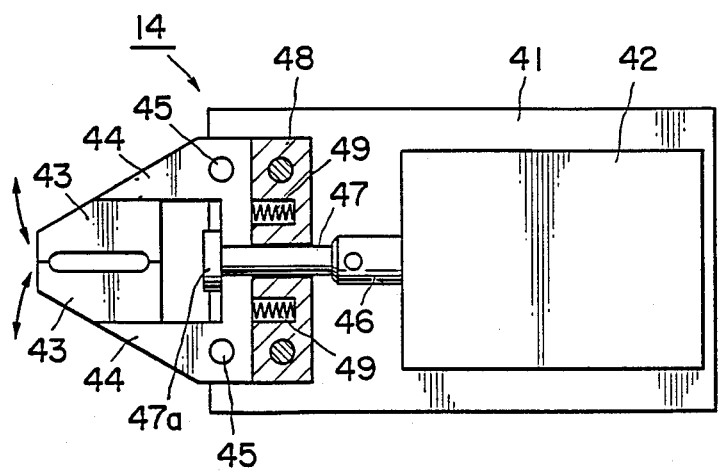
FIG. 5 is a top plan view, partly in section, of the shaker mechanism.

FIG. 4 and 5 show the details of the shaker mechanism 14. It takes the form of a gripper mechanism 39 which operates to periodically grip and squeeze a hose 40 of elastic or pliant material forming a part of the delivery conduit 12, FIG. 1. The gripper mechanism 39 comprises a pair of L-shaped gripping jaws 44 having a pair of teeth 43 which are disposed on opposite sides of the hose 40 and which are periodically actuated toward and away from each other by intermittent energization of a solenoid 42 on a standard 41. The pair of gripping jaws 44 are mounted on upstanding pins 45 for pivotal motion in a horizontal plane. The solenoid 42 has a plunger 46 coupled to a link 47 which has a flange 47a on its end away from the solenoid. The flange 47a engages the pair of gripping jaws 44 in such a manner that upon energization of the solenoid 42, the retracting plunger 46 causes the gripping jaws 44 to jointly pivot in opposite directions, resulting in the movement of the pair of teeth 43 toward each other. A pair of helical compression springs 49 are mounted respectively between the gripping jaws 44 and a fixed support 48 on the standard 41, biasing the gripping jaws in such directions that the pair of teeth 43 tend to travel apart from each other.

Figure 6:
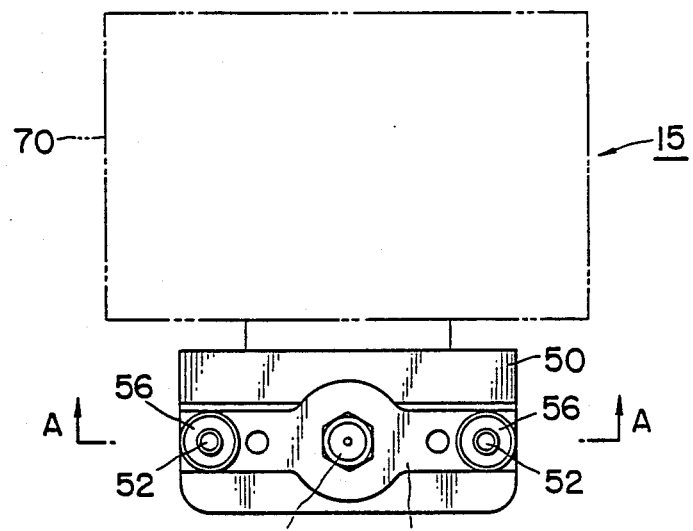
FIG. 6 is a top plan view of the embedding box holder.
Figures 7, 8:
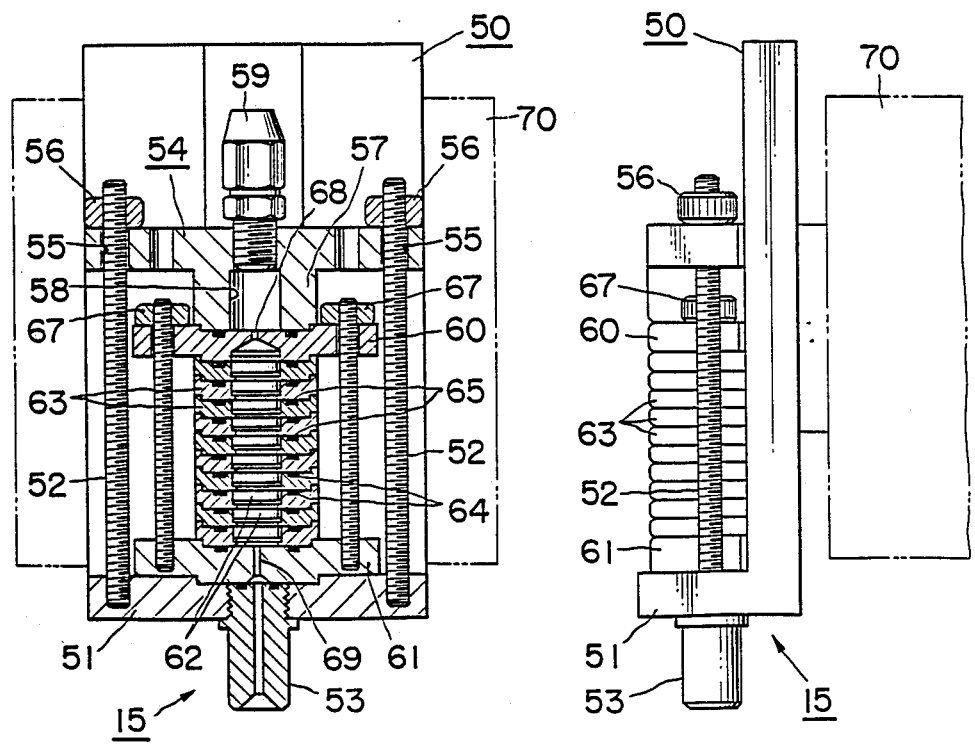
FIG. 7 is a sectional view of the embedding box holder taken along the line A—A of FIG. 6.
FIG. 8 is an elevation of the embedding box holder as seen from the right hand side of FIG. 7.

The embedding box holder 15 is illustrated in detail in FIGS. 6–8. Seen at 50 is an upstanding baseplate fabricated from metal, typically aluminum, that is a good conductor of heat. The baseplate 50 has a horizontal ledge 51 formed on its bottom end. A pair of threaded studs 52 are erected on the ledge 51 with a spacing therebetween. Also mounted to the ledge 51, in a position intermediate the pair of studs 52, is a bottom fitting 53 extending downwardly therefrom for communicative connection of the top end of the delivery conduit 12 to the embedding box holder 15.

Extending upwardly from the baseplate ledge 51, the pair of threaded studs 52 have their top end portions inserted in and through holes 55 defined in a yoke 54 of generally T-shaped vertical section in the vicinities of its opposite ends. Nuts 56 are fitted over the top ends of the studs 52 protruding upwardly of the yoke 54. The yoke 54 has a thickened midportion 57 with a fluid passageway 58 defined vertically therethrough. A top fitting 59 is firmly inserted in this passageway 58 from above for communicative connection of one end of the overflow conduit 17, FIG. 1, to the embedding box holder 15.

A plurality of substantially annular box carriers 63, each having an embedding box 62 mounted fast therein, are stacked, via a pair of holder plates 60 and 61, between the baseplate ledge 51, having the lower fitting 53, and the yoke 54 having the top fitting 59. The box carriers 63 are so shaped as to be firmly stacked up, and O-ring seals 65 are fitted in annular grooves 64 formed in their top surfaces to seal the joints between the box carriers against the leakage of the reagent. The embedding boxes 62 within their carriers 63 are each in the shape of a short cylinder of a plastic or like material, complete with a meshed or open-worked bottom which is permeable to the reagent but which blocks the passage of the specimens to be embedded.

The stack of box carriers 63 carrying the embedding boxes 62 of the foregoing construction are immovably captured between the pair of holder plates 60 and 61. For thus holding the stack of box carriers 63, the lower holder plate 61 has a pair of threaded studs 66 extending upwardly therefrom and inserted in and through holes in the upper holder plate 60. Nuts 67 are tightened on the top end portions of the threaded studs 66 as they protrude from the holes in the upper holder plate 60.

Fluid passageways 68 and 69 are formed in and through the holder plates 60 and 61, respectively, to establish communication between the interiors of the embedding boxes 62 and the passageway 58 in the yoke 54 as well as the passageway in the bottom fitting 53. It is to be noted that despite the showing of FIGS. 6–8, the embedding boxes 62 and their carriers 63 need not constitute separate units but can be of integral construction. Shown at 70 in FIGS. 6–8 is a thermostatic module of any known or suitable construction, preferably containing a thermoelectric refrigerator working on the Peltier effect for heating and cooling the specimens as well as the reagent that has been pumped into the embedding boxes 62.

The following is a discussion of a method of embedding desired objects of microscopic examination in a resin material by the micrological apparatus of the foregoing construction having the embedding boxes 62 mounted to the embedding box holder 15. First, loaded with the embedding boxes 62 containing the specimens to be embedded, the box carriers 63 may be stacked up thereby providing a tubular arrangement of the embedding boxes 62 for the flow of a liquid therethrough. Then the stack of the loaded box carriers 63 may be mounted firmly between the pair of holder plates 60 and 61 by tightening the nuts 67 on the studs 66. Then the stack of the loaded box carriers 63 with the holder plates 60 and 61 may be mounted fast between the baseplate ledge 51 and the yoke 54 by tightening the nuts 56 on the studs 52. Now the mounting of the embedding boxes to the holder 15 has been completed.

Then the delivery pump 13 on the delivery conduit 12 may be set into operation for delivering a selected reagent from either of the receptacles 7a, 7b and 7c into the embedding boxes 62 in the holder 15 by way of the delivery conduit 12, lower fitting 53 and passageway 69. The specimens within the embedding boxes 62 will be immersed in the selected reagent so delivered to the embedding box holder 15. The delivery pump 13 should be held out of operation during the impregnation of the specimens with the reagent.

During the time the delivery pump 13 is so held out of operation, the reagent select mechanism 9 may be driven for placing the delivery conduit 12 in communication with the waste liquid conduit 25. The reagent select mechanism 9 can be driven as, with the solenoid 30 energized to raise the reciprocator 34 against the force of the compression spring 35 and hence to disengage the plug 37 from the socket member 38, the motor 27 is set into rotation for revolving the rotary post 29. The motor 27 may be set out of rotation as the plug 37 reaches a position of vertical register with that one of the socket members 38 which has the waste liquid conduit 25 coupled thereto. Then the solenoid 30 may be de-energized to permit the plug 37 to move into fluid-tight engagement with the required socket member 38 under the bias of the compression spring 35.

Also, while the delivery pump 13 is held out of operation as above stated, the solenoid 42 of the shaker mechanism 14 may be excited intermittently thereby imparting vibration to the reagent within the embedding boxes 62 and hence expediting the infiltration of the reagent into the specimens. Each time the solenoid 42 is excited, the pair of gripping jaws 44 will pivot against the forces of the compression springs 49, with the consequent constriction of the pliant hose 40 by the pair of teeth 43. The constriction of the pliant hose 40 will cause part of the reagent on the downstream side of the shaker mechanism 14 to flow into the enlargement 16, which in this particular embodiment is formed by the fluid passageway 58 of relatively large cross section in the yoke 54. Then, upon de-energization of the solenoid 42, the pair of gripping jaws 44 will pivot away from each other owing to the forces of the compression springs 49. The hose 40 will then expand by virtue of its own elasticity to cause reverse flow of the reagent from its downstream side. The repeated energization and de-energization of the solenoid 42 at fine intervals will lead to the ready permeation of the reagent through the specimens.

Following the shaking of the reagent for a preassigned length of time and, consequently, the complete impregnation of the specimens with the reagent, the delivery pump 13 may be set into rotation in a reverse direction for the discharge of the excess reagent into the waste receptacle 18. For such discharge of the used reagent the three-way valve 19 should be actuated to place the waste receptacle 18 in communication with the air filter 21. Air will then be delivered to the embedding boxes 15 by way of the overflow conduit 17 for smooth discharge of the used reagent.

The vacuum pump 22 provided to the waste receptacle 18 serves the purpose of evacuating the embedding box holder 15 as when the specimens within the embedding boses are being treated with glutaraldehyde or embedded in a resin. The exhaust gases produced during the operation of the vacuum pump 22 are cleaned as they pass through the activated charcoal filter 24.

Upon completion of the discharge of the used reagent, the reagent select mechanism 9 may be re-actuated for placing the delivery conduit 12 in communication with some other of the reagent receptacles 7a, 7b or 7c containing another desired reagent. This second selected reagent will be fed into the embedding boxes 62 as the delivery pump 13 is again set into rotation in a forward direction.

The foregoing cycle of operation may be repeated for the embedment of the specimens within the embedding boxes 62. For treating the specimens with an alcohol of progressively greater concentrations, a lower concentration (e.g. 50%) alcohol may first be supplied to the embedding boxes 62. Then, with this lower concentration alcohol left undischarged, a higher concentration (e.g. 100%) alcohol may be supplied to the embedding boxes 62. The alcohol concentration within the embedding boxes 62 will become gradually higher as the excess amount is discharged through the overflow conduit 17.

Such being the construction and operation of the apparatus in accordance with the invention, it will be appreciated that only minimal amounts of reagents are required for the embodment of the specimens, and the running costs of the apparatus will also be reduced to a minimum. Further, instead of dipping the specimens in the reagents, the reagents are pumped into the embedding boxes in their holder in accordance with the invention. This makes it possible to treat the specimens with an alcohol of various concentrations merely by intermingling two alcohol preparations of 50% and 100% concentrations which are available commercially, without the need for the provision of alcohol preparations of many different concentrations. Still further, the specimens will be favorably embedded as the reagents and resin are positively fed into the embedding boxes.

INDUSTRIAL APPLICABILITY

Objects of microscopic examination can be efficiently embedded in a resin or like material, so that the invention finds application in medical and scientific fields for the examination of living tissues or the like.

I claim:

1. Apparatus for the preparation of objects for microscopic examination comprising a reagent housing, a plurality of reagent receptacles placed in said housing for containing different reagents for treating specimens, a delivery pump capable of bidirectional rotation and of blocking the flow of a reagent therethrough when out of operation, a reagent select mechanism connected between said reagent housing and said delivery pump for placing any selected one of said reagent receptacles in communication with said delivery pump, an embedding box holder for holding in a stack a plurality of embedding boxes containing specimens for microscopic examination, said delivery pump being connected to said embedding box holder for causing any selected reagent to flow through said embedding boxes, and a reagent shaker mechanism, provided between said embedding box holder and said delivery pump, said shaker mechanism having means for causing repeated forward and backward vertical flows through said embedding box holder, at closely spaced intervals, of the selected reagent in the embedding box holder while the delivery pump is out of operation.

2. Apparatus for the preparation of objects for microscopic examination as claimed in claim 1, wherein said embedding box holder is elongated vertically for holding a vertical stack of embedding boxes.

3. Apparatus for the preparation of objects for microscopic examination as claimed in claim 1, wherein said embedding box holder comprises an upstanding baseplate holding a plurality of annular box carriers fluid-tightly stacked up, each box carrier having mounted thereto one of the embedding boxes, and holder means for holding the stack of box carriers.

4. Apparatus for the preparation of objects for microscopic examination as claimed in claim 1, wherein said reagent select mechanism comprises a table having a plurality of socket members communicating with said separate reagent receptacles via suction conduits, a rotary post rotatably mounted on said table, and plug reciprocator means for vertically reciprocating a plug into and out of selective engagement with said socket members, said plug communicating with said delivery pump via a delivery conduit.

5. Apparatus for the preparation of objects for microscopic examination as claimed in claim 1, wherein said embedding box holder communicates with a waste receptacle via an overflow conduit having a portion of enlarged cross section, said waste receptacle communicating with one of socket members of said reagent select mechanism via a waste liquid conduit.

6. Apparatus for the preparation of objects for microscopic examination comprising an embedding box holder, a stack of embedding boxes contained in said holder and each containing a specimen, a pump for selectively delivering reagents to said stack of embedding boxes, a reagent shaker mechanism disposed under said stack of embedding boxes for vibrating a reagent within the embedding box holder holding said stack of embedding boxes, said reagent shaker mechanism comprising a pair of gripping jaws for cyclically gripping and releasing a conduit through which said reagents are fed to said stack of embedding boxes, and drive means for driving said pair of gripping jaws.

7. Apparatus for the preparation of objects for microscopic examination as claimed in claim 6, wherein said embedding box holder includes an upstanding baseplate holding a plurality of annular box carriers fluid-tightly stacked up, each box carrier having mounted thereto one of the embedding boxes, and holder means for holding the stack of box carrier.

8. Apparatus for the preparation of objects for microscopic examination as claimed in claim 6, wherein said apparatus further comprises a reagent select mechanism for selectively supplying the reagents to said stack of embedding boxes, said reagent select mechanism comprising a table having a plurality of socket members communicating with separate reagent receptacles via suction conduits, a rotary post rotatably mounted on said table, and plug reciprocator means for vertically reciprocating a plug into and out of selective engagement with said socket members, said plug communicating with said delivery pump via a delivery conduit.

9. Apparatus for the preparation of objects for microscopic examination comprising a reagent housing, a plurality of reagent receptacles placed in said housing for containing different reagents for treating specimens, a delivery pump capable of bidirectional rotation and of blocking the flow of a reagent therethrough when out of operation, a reagent select mechanism connected between said reagent housing and said delivery pump for placing any selected one of said reagent receptacles in communication with said delivery pump, a vertically elongated embedding box holder for holding in a stack a plurality of embedding boxes containing specimens for microscopic examination, said delivery pump communicating with said embedding box holder via an elastic conduit for causing any selected reagent to flow through said embedding boxes, and a reagent shaker mechanism provided under said embedding box holder for shaking the reagent within said embedding box holder, said reagent shaker mechanism comprising a pair of gripping jaws for cyclically gripping and releasing said elastic conduit, and drive means for driving said pair of gripping jaws.

* * * * *